United States Patent [19]

Honda et al.

[11] Patent Number: 5,621,084
[45] Date of Patent: Apr. 15, 1997

[54] PROCESS FOR REMOVAL OF ALLYL GROUP OR ALLYLOXYCARBONYL GROUP

[75] Inventors: Msanori Honda, Handa; Hiromasa Morita, Chita; Isao Nagakura, Aichi-ken, all of Japan

[73] Assignee: Pfizer Inc., New York, N.Y.

[21] Appl. No.: 417,285

[22] Filed: Apr. 3, 1995

[51] Int. Cl.$^6$ .............................. C07H 1/06; C07C 29/10; C07C 41/00; C07K 1/00
[52] U.S. Cl. .................. 536/1.11; 536/4.1; 536/18.5; 536/27.12; 536/120; 536/124; 536/127; 568/672; 568/700; 530/344
[58] Field of Search .................... 536/1.11, 4.1, 536/18.5, 27.12, 124, 127, 120; 568/672, 700; 530/344

[56] References Cited

U.S. PATENT DOCUMENTS

| 4,314,942 | 2/1982 | McCombie | 568/830 |
| 4,910,019 | 3/1990 | McCaleb | 424/442 |

FOREIGN PATENT DOCUMENTS

| 410727 | 7/1990 | European Pat. Off. . |
| 0441489 | 2/1992 | Japan . |
| 6220054 | 8/1994 | Japan . |
| 6321952 | 11/1994 | Japan . |

OTHER PUBLICATIONS

McCombie et al., Journal of Organic Chemistry, 1982, 47, 587.

Primary Examiner—John Kight
Assistant Examiner—Everett White
Attorney, Agent, or Firm—Peter C. Richardson; Gregg C. Benson; Robert T. Ronau

[57] ABSTRACT

This invention relates to a process for the removal of an allyl or allyloxycarbonyl group from an allyl or allyloxycarbonyl group protected compound (such as an allylic ester, carbonate, carbamate, O-allyl derivatives or N-allyl derivatives), which comprises contacting the allyl or allyloxycarbonyl group protected compound with a sulfinic acid compound, in the presence of a palladium catalyst in a reaction-inert solvent. Preferably, the sulfinic acid compound is represented by the formula:

$$X-SO_2M \qquad (I)$$

wherein X is $C_{1-20}$ alkyl, substituted $C_{1-20}$ alkyl (wherein the substituent(s) are independently halo, nitro, sulfo, oxo, amino, cyano, carboxy, hydroxy or moieties derived therefrom), phenyl, substituted phenyl (wherein the substituent(s) are independently $C_{1-3}$ alkyl, halo nitro, sulfo, oxo, amino, cyano, carboxy, hydroxy, acetamido or moieties derived therefrom), furyl or thienyl; and M is hydrogen, an alkali metal or ammonium salt residue. Of these, most preferred sulfinic acid compound is lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid or ammonium benzenesulfinate. This invention is well suited to a process for the conversion of an allyl ester of 5R,6S-6-(1R-hydroxyethyl)-2-(1R-oxo-3S-thiolanylthio)-2-penem-3-carboxylic acid to 5R,6S-6-(1R-hydroxyethyl)-2-(1R-oxo-3S-thiolanylthio)-2-penem-3-carboxylic acid.

28 Claims, No Drawings

PROCESS FOR REMOVAL OF ALLYL GROUP OR ALLYLOXYCARBONYL GROUP

BACKGROUND OF THE INVENTION

The present invention relates to an improved chemical process for the removal of an allyl or allyloxycarbonyl group from an allyl or allyloxycarbonyl group protected compound (such as an allylic ester, carbonate, carbamate, O-allyl derivatives or N-allyl derivatives). This process comprises contacting the allyl or allyloxycarbonyl group protected compound with a sulfinic acid compound, in the presence of a palladium catalyst in a reaction-inert solvent.

Allyl groups have been frequently used as protecting groups for a carboxyl group or the like in the synthesis of beta-lactam antibiotics. The advantages of the use of the allyl groups in the synthesis of beta-lactam antibiotics have been reported by S. W. McCombie et al. [J. Org. Chem., 47, 587 (1982)]. The removal of an allyl group from an allylic ester or the like has been reported in several literature and patent gazettes.

Japanese Patent Application Publication No. S60-9730 (U.S. Pat. No. 4,314,942) discloses a process for the removal of an allyl group in an allylic ester or an allyloxycarbonyl group in an allylic carbonate or carbamate by reaction with 2-ethylhexanoic acid or an alkali metal salt thereof in the presence of an organic-soluble palladium complex catalyst.

Japanese Patent Application Laid-Open No. H03-130293 (EP 410727A1) describes a process for removing an allyl group from a penem compound by reaction with a cyclic 1,3-diketone compound, such as dimedone, or its alkali metal enolate. Japanese Patent Application Laid-Open No. H04-41489 discloses a similar process using an alkali metal salt of a carboxylic acid having 1 to 4 carbon atoms.

However, according to the above conventional methods, the yield of the final reaction product was not always high. For example, in the conventional methods, the activity of catalyst was lowered by using crude raw materials, and the yield was lowered in the treatment of compound which is sensitive to the basic condition of the protecting group.

On the other hand, O-allylethers and N-allyl derivatives of amino group are stable in a nucleophilic reaction and electrophilic reaction. Thus, protection of a hydroxy group by using O-allylether or protection of an amino group by using N-allyl derivative is considered useful in a variety of synthesis for biologically active compounds. However the allyl protection has not been frequently used in this field, because deprotection of the allyl group from O-allylether or N-allyl derivative could not be done under mild conditions.

Japanese Patent Application Publication No. H02-262542 (USP409100019) discloses a process for the removal of an allyl group in a N-allylaniline in the presence of palladium or cupper complex catalyst. In this process, however, considerably severe condition are required.

Therefore, it would be desired if a method of removing an allyl group or the like from a variety of compounds having an allyl group or the like such as an allylic ester, carbonate, carbamate, O-allyl derivatives or N-allyl derivatives were provided, with excellent yield, in a highly chemoselective manner without affecting any rest of functional groups attached to the compounds to be treated.

SUMMARY OF THE INVENTION

The present invention provides a process for the removal of an allyl or allyloxycarbonyl group from an allyl or allyloxycarbonyl group protected compound, which comprises contacting the allyl or allyloxycarbonyl group protected compound with a sulfinic acid compound, in the presence of a palladium catalyst in a reaction-inert solvent.

Preferably, the present invention provides a process for the conversion of an allyl ester of a carboxylic acid to the carboxylic acid, an allyloxycarbonyl derivative of an alcohol to the alcohol or an allyloxycarbonyl derivative of an amine to the amine, which comprises contacting the allyl ester of a carboxylic acid, the allyloxycarbonyl derivative of an alcohol or the allyloxycarbonyl derivative of an amine with a sulfinic acid compound, in the presence of a palladium catalyst in a reaction-inert solvent.

Also preferably, the present invention provides a process for the conversion of an O-allylether of an alcohol to the alcohol, an N-allyl derivative of a compound containing amino group to the compound containing amino group or O-allyl derivative of an oxime to the oxime, which comprises contacting the O-allylether of an alcohol, N-allyl derivative of a compound containing amino group or O-allyl derivative of an oxime, with a sulfinic acid compound, in the presence of a palladium catalyst in a reaction-inert solvent.

According to the process of the present invention, deprotection of an allyl or allyloxycarbonyl group from an allylic ester, carbonate, carbamate, an O-allylether of an alcohol, N-allyl derivative of a compound containing amino group or O-allyl derivative of an oxime can be effectively achieved, with excellent yield, in a highly chemoselective manner without affecting any rest of functional groups attached to the compounds to be treated. The present process is particularly well suited to the removal of allyl and allyloxycarbonyl protecting groups in the presence of the beta-lactam group found in natural, biosynthetic, semisynthetic and synthetic beta-lactam antibiotic compounds. As compared to the conventional methods using sodium 2-ethylhexanoate or dimedone, the process of the present invention can be used in a wider range of areas where deprotection of an allyl or allyloxycarbonyl group is needed. Also, the deprotecting agents used in the present invention are generally less expensive and thus can be effectively used on a large scale production which use crude allyl compounds as raw materials.

DETAILED DESCRIPTION OF THE INVENTION

The present invention will be described in more detail below.

The present invention is characterized by the use of a sulfinic acid compound as a deprotecting agent, to remove an allyl or allyloxycarbonyl group from an allylic ester, carbonate, carbamate, an O-allylether of an alcohol, N-allyl derivative of a compound containing amino group or O-allyl derivative of an oxime to be treated. Sulfinic acid compounds which can be used in the present invention include aliphatic, alicyclic, aromatic and heteroaromatic sulfinic acids and salts thereof.

Suitable sulfinic acid compounds are those represented by the formula:

$$X\text{—}SO_2M \qquad (I)$$

wherein X is $C_{1-20}$ alkyl, substituted $C_{1-20}$ alkyl (wherein the substituent(s) are independently halo, nitro, sulfo, oxo, amino, cyano, carboxy, hydroxy or moieties derived therefrom), phenyl, substituted phenyl (wherein the substituent(s) are independently $C_{1-3}$ alkyl, halo, nitro, sulfo, oxo, amino, cyano, carboxy, hydroxy, acetamido or moieties derived therefrom), furyl or thienyl; and M is hydrogen, an alkali metal or ammonium salt residue. The moieties derived from halo, nitro, sulfo, oxo, amino, cyano, carboxy or hydroxy are used herein to mean those easily formed by a reaction between these groups and a compound having a group reactable therewith (e.g., ester residues in the case of carboxy, amide residues in the case of amino, and ether residues in the case of hydroxy).

More suitable sulfinic acid compounds are those compounds of Formula (I) wherein X is $C_{1-16}$ alkyl, substituted $C_{1-16}$ alkyl (wherein the substituent(s) are independently halo, nitro, sulfo, oxo, amino, cyano, carboxy, hydroxy or moieties derived therefrom), phenyl, substituted phenyl (wherein the substituent(s) are independently $C_{1-3}$ alkyl, halo, nitro, sulfo, oxo, amino, cyano, carboxy, hydroxy, acetamido or moiety derived from therefrom), furan or thiophene, preferably mono- or di-substituted phenyl; and M is hydrogen, an alkali metal, ammonium or ammonium salt residue. Particularly suitable sulfinic acid compounds of formula (I) are those mono- or disubstituted phenyl sulfinic acid compounds of formula (I) wherein X is phenyl or methylphenyl; and M is an alkali metal such as lithium, sodium or potassium, or an ammonium salt residue (a residue of ammonia, primary amine, secondary amine, tertiary amine or quaternary ammonium salt).

Also, suitable sulfinic acid compounds of formula (I) include those $C_{1-20}$ (preferably $C_{1-10}$) alkyl substituted sulfinic acid compounds such as methylsulfinic acid, ethylsulfinic acid, isobutylsulfinic acid, octylsulfinic acid, octadecylsulfinic acid, and their salts. The alkyl group attached to sulfinic acid compound may be substituted with one or two substituents such as halo and hydroxy as far as such substituents do not interfere with the deprotection reaction. Examples of such compounds include sodium hydroxymethanesulfinate.

Of these, preferred compounds are lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid, ammonium benzenesulfinate, tetrabutylammonium benzenesulfinate, sodium p-carboxybenzenesulfinate, sodium octylsulfinate, sodium ethylsulfinate, sodium 4-chloro-3-nitrobenzenesulfinate, sodium 4-acetamidobenzenesulfinate, sodium thiophene-2-sulfinate, sodium methylsulfinate, sodium isobutylsulfinate, sodium hexadecylsulfinate, sodium hydroxymethanesulfinate, ammonium p-toluenesulfinate, triethylammonium p-toluenesulfinate or tetrabutylammonium benzenesulfinate.

Of these, more preferred compounds are lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid or ammonium benzenesulfinate.

The deprotecting agent used in the present invention may be used in an amount of from 0.5 to 5 equivalent, preferably from 1.0 to 1.2 equivalent, against the allylic ester, carbonate, carbamate, N-allyl derivatives or O-allyl derivatives to be treated.

"Allyl or allyloxycarbonyl groups" as used herein mean any groups having an allylic structure, and which are removal by the process of the present invention. "Allyl" as used herein means an alkyl or substituted alkyl group having a carbon-carbon double bond at the 2,3-position. Examples of the "allyl groups" are allyl, methylallyl, crotyl, chloroallyl and cinnamyl. Examples of the "allyloxycarbonyl" groups are allyloxycarbonyl, methylallyloxycarbonyl, crotyloxycarbonyl, chloroallyoxycarbonyl and cinnamyloxycarbonyl. Suitable allyl or allyloxycarbonyl groups are those present in known allylic alcohols or activated esters thereof which are used to protect the carboxy, hydroxy or amino groups. Suitable allylic alcohols are those such as allyl alcohol, haloallyl alcohol, methylallyl alcohol, crotyl alcohol, cinnamyl alcohol or the activated esters thereof. Thus, preferred compounds to be treated are the allylic esters, carbonates, carbamates and O-allyl derivatives wherein the allyl group or allyloxycarbonyl group is derived from allyl alcohol. "Hydroxy group" as used herein means —OH in organic compound. Examples of the "hydroxy group" are —OH in alcohol, —OH in phenol, —OH in oxime and —OH in glycoside.

Preferred compounds from which an allyl protecting group can be detached, are beta-lactam allylic esters such as the allylic esters of penams, e.g., penicillin G and ampicillin; cephems, e.g., cephalosporanic acid, 7-(phenylacetamido)desacetoxycephalosporanic acid and cephamycin; carbapenems, e.g., thienamycin; and penems, e.g., 5R,6S-6-(1R-hydroxyethyl)-2-(1R-oxo-3S-thiolanylthio)-2-penem-3-carboxylic acid.

The process of the present invention is well suited for the conversion of allyl esters of 5R,6S-6-(1R-hydroxyethyl)-2-(1R-oxo-3S-thiolanylthio)-2-penem-3-carboxylic acid to 5R,6S-6-(1R-hydroxyethyl)-2-(1R-oxo-3S-thiolanylthio)-2-penem-3-carboxylic acid.

Preferably the O-allylether are, for example, polyether, macrolide, oligosaccharide or glycoside in which their hydroxy groups are protected by allyl group, and especially preferred compound is 3-O-allyl-1,2:5,6-di-O-isopropylidene-α-D-glucofuranose. Examples of O-allyl derivative of an oxime are polyether, macrolide, oligosaccharide or glycoside in which their hydroxy groups are protected by allyl group, and especially preferred compound is (2E,4E,8E)-(4'R,5'S,6S ,6'R,7S,11R,13S,15S,17aR,20aR,20bS)-6'-cyclohexyl-4'20b-dihydroxy-20-(2-propenyloxyimino)-5',6, 8,19-tetramethyl-3',5',6,6',7,10,11,14,15,17a,20,20a,20b-tridecahydro-17-oxospiro[11,15-methano-2H, 13H, 17H-furo[4,3,2-pq][2,6]benzodioxacyclooctadecine-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside. Examples of N-allyl derivative of a compound containing amino group are alkaloid, nucleoside or peptide in which their amino groups are protected by an allyl group, and especially preferred compound is N-allyl-N-pentylphenylamine.

The process of the present invention is well suited for the conversion of 3-O-allyl-1,2:5,6-di-O-isopropylidene-α-D-glucofuranose to 1,2:5,6-di-O-isopropylidene-α-D-glucofuranose, N-allyl-N-pentylphenylamine to N-pentylphenylamine, or (2aE,4E,8E)-(4'R,5'S,6S,6'R,7S,11R,13S,15S, 17aR,20aR,20bS)-6'-cyclohexyl-4'20b-dihydroxy-20-(2-propenyloxyimino)-5',6,8,19-tetramethyl-3',5',6,6',7,10,11, 14,15,17a,20,20a,20b-tridecahydro-17-oxospiro[11,15-methano-2H, 13H, 17H-furo[4,3,2pq][2,6] benzodioxacyclooctadecin-13,2'-[2H]piran]-7-yl 2,6-dideoxy-4-O-(2,6-dideoxy-3-O-methyl-α-L-arabino-hexapyranosil)-3-O-methyl-α-L-arabino-hexapyranoside to (2aE,4E,8E)-(4'R,5'S,6S,6'R,7S,11R,13S,15S,17aR,20aR, 20bS)-6'-cyclohexyl-4'-20b-dihydroxy-20-(hydroxyimino)-5',6,8,19-tetramethyl-3',5'6,6',7,10,11,14,15,17a,20,20a, 20b-tridecahydro-17-oxospiro[11,15-methano-2H, 13H, 17H-furo[4,3,2pq][2,6]benzodioxacyclooctadecin-13,2'-[2H]pyran]-7-yl=2,6-dideoxy-4-O-(2,6-dideoxy-3-O-methyl-α-L-arabino-hexopyranosyl)-3-O-methyl-α-L-arabino-hexopyranoside.

Also, another preferred group of compounds to be treated by the process of the present invention include allylic esters of amino acids such as glycine, serine and phenylalanine; and allylic esters of benzoic acid and nalidixic acid.

Further, allylic carbonates which can be treated by the present invention include, for example, derivatives of alcohols such as n-octadecanol, 1-menthol, 1-octanol, 2-octanol, 1-adamantanol and N-benzyloxycarbonylserine; steroids such as cholesterol, cortisone, testosterone and estradiol; phenols such as 1-naphthol; and macrolides such as erthromycin and rosamicin. Allylic carbamates which can be treated by the process of the present invention include, for example, those derived from amines such as 1-aminoadamantane, 2-octylamine, ephedrine, aniline, p-methoxyaniline, 1-naphthylamine and benzocaine; and amino acids such as glycine, phenylalanine and serine.

In the practice of the present invention, the allyl or allyloxycarbonyl group-deprotection reaction is carried out in the presence of a palladium complex catalyst. Suitable palladium catalysts are those palladium compounds capable of easily forming a π-allyl complex when reacted with an allyl compound. More suitable palladium catalysts are those having a ligand such as tetrakis(triphenylphosphine)palladium(0), dichlorobis(triphenylphosphine)palladium (II), dichlorobis(acetonitrile)palladium (II) and dichlorobis(triisopropoxyphosphine)palladium (II) or palladium (II) diacetate in conjunction with triphenylphosphine or triethyl phosphite (Refer to Jiro Tsuji, "Transition Metals in Organic Synthesis", Kagakudojin, 1991). In a conventional method using sodium 2-ethylhaxanoate as a deprotecting agent, during the reaction, supplemental addition of triphenylphosphine or a palladium complex catalyst is usually required to accelerate the deprotection reaction or to keep the catalytic activity high. However, in the process of the present invention, the addition of such a phosphine compound or the supplemental catalyst is not necessarily required because of good catalytic activity and high reaction speed in the present reaction system. The palladium complex catalyst may be utilized in an amount sufficient to catalyze the deprotection reaction, generally in an amount of from 0.1 to 20 mole percent, preferably from 2 to 7 mole percent, of the allylic ester, carbonate, carbamate, N-allyl derivatives or O-allyl derivatives to be treated.

The deprotection reaction is carried out in a suitable reaction-inert solvent. Suitable solvents include hydroxy group-containing solvents such as alcohols, e.g., methanol and ethanol, and water; and non-hydroxylic solvents include, for example, haloalkyl compounds such as dichloromethane and chloroform; esters such as methyl acetate and ethyl acetate; ethers such as diethyl ether and tetrahydrofuran; nitriles such as acetonitrile and propionitrile; ketones such as acetone and methyl ethyl ketone; and aromatic hydrocarbons such as benzene and toluene; and a mixture thereof. In the case of using sodium p-toluenesulfinate, methanol or water may be used together with tetrahydrofuran or the like.

The deprotection reaction may be carried out under substantially neutral conditions. Thus, the process of the present invention is useful in the synthesis using starting materials and final compounds which are sensitive to acidic or basic conditions.

Conditions for the deprotection reaction may be determined depending upon the kind of compounds to be treated, deprotecting agents, catalysts, solvents used, etc. In general, the deprotection reaction may be carried out at a temperature of from −20° C. to 100° C., preferably from 10° C. to 40° C. for from 1 min. to 18 hours, preferably from 5 min. to 6 hours.

Typical procedures for removing an allyl or allyloxycarbonyl group are described below. The following procedures are for illustrative purposes, and do not restrict the scope of the present invention.

First, an allylic ester, carbonate, carbamate, O-allylether of an alcohol, N-allyl derivative of a compound containing amino group or O-allyl derivative of an oxime to be treated, and a palladium catalyst, are dissolved or suspended to a suitable solvent such as tetrahydrofuran or methylene chloride. The deprotecting agent is added to the mixture containing the compound to be treated and the catalyst. The reaction mixture is stirred at an appropriate temperature for time sufficient to complete the deprotection reaction.

If the product of the present process is scarcely soluble in the solvent, the product precipitates as crystals, and the target salt can be collected by filtration. If the product of the process is difficult to precipitate from the resulting reaction mixture, the mixture is thoroughly mixed with the solvent used in the reaction and another solvent in which the product is scarcely soluble to effect the precipitation of the crystals. Alternatively, hydrochloric acid is added to the solution containing the product of the present process to effect the precipitation of the crystals, and then the crystals are filtered off by known filtration techniques.

The present invention will be described in more detail with reference to the following Examples and Comparative Examples.

EXAMPLES

Example 1

Removal of 2-Chloro-2-Propenyl From 2-Chloro-2-propenyl 5R,6S 6-(1R-Hydroxyethyl)-2-(1R-oxo-3S-thiolanylthio)-2-penem-3-carboxylate:

A solution of sodium p-toluenesulfinate tetrahydrate (155 mg, 0.615 mmol) in methanol (2.3 ml) was added at room temperature to a suspension of 2-chloro-2-propenyl 5R,6S-6-(1R-hydroxyethyl)-2-(1R-oxo-3S-thiolanylthio)-2-penem-3-carboxylate (261 mg, 0.615 mmol) prepared in preparation 1 and tetrakis(triphenylphosphine)palladium (41.7 mg, 36.1 μmol) in tetrahydrofuran (3.9 ml). The reaction mixture was stirred at room temperature for 105 minutes and ethyl acetate (12 ml) was added dropwise to precipitate the sodium salt of the target compound. Celite (0.8 g) was added to the mixture. After filtration, the precipitates and celite were washed with ethyl acetate (3 ml+1.5 ml×3) and the precipitates were dissolved in water (3 ml+1.5 ml×3). The aqueous solution was acidified with an ion-exchange resin (Manufactured by Mitsubishi Chem. under the trade name of DIAION PK216H) and acetone (7.5 ml) was added. The resin was filtered off and washed with acetone-water (2:1, 1.5 ml×3). The combined filtrates were concentrated at 24° C. by an evaporator to strip acetone and freeze-dried to give light yellow powders (209 mg) in 97% yield.

Comparative Example 1

The procedures of Example 1 were repeated except that the following reactants, catalyst and solvent were used.

Sodium 2-ethylhexanoate: 20 mg (0.14 mmol)

2-Chloro-2-propenyl 5R,6S-6-(1R-hydroxyethyl)-2-(1R-oxo-3S-thiolanylthio)-2-penem-3-carboxylate: 50 mg (0.118 mmol)

Palladium diacetate: 5.6 mg (24.9 μmol)

Triethylphosphite: 39 mg (0.234 mmol)

Acetone: 10 ml

As a result, 5 mg of light yellow powders were obtained in 13% yield.

Example 2

Removal of 2-Propenyl from 2-Propenyl5R,6S-6-(1R-hydroxyethyl)-2-(1R-oxo-3S-thiolanylthio)-2-penem-3-carboxylate:

A solution of sodium p-toluenesulfinate tetrahydrate (352 mg, 1.41 mmol) in methanol (3.5 ml) was added at room temperature to a suspension of 2-propenyl 5R,6S-6-(1R-hydroxyethyl)-2-(1R-oxo-3S-thiolanylthio)-2-penem-3-carboxylate (500 mg, 1.28 mmol) prepared in Preparation 2 and tetrakis(triphenylphosphine)palladium (104 mg, 89.8 μmol) in tetrahydrofuran (8.5 ml). The reaction mixture was stirred at room temperature for 35 minutes and ethyl acetate (25 ml) was added dropwise to precipitate the sodium salt of the target compound. Celite (1 g) was added to the mixture. After filtration, the precipitates and celite were washed three times with ethyl acetate (3 ml×3) and the precipitates were dissolved in water (5 ml+2 ml×3). The aqueous solution was acidified with an ion-exchange resin (Manufactured by Mitsubishi Chem. under the trade name of DIAION PK216H) and acetone (17 ml) was added. The resin was filtered off and washed with three times acetone-water (2:1, 2 ml×3). The combined filtrates were concentrated at 20° C. by an evaporator to strip acetone and freeze-dried to give light yellow powders (405 mg) in 90% yield.

Example 3

Removal of 2-Methyl-2-Propenyl From 2-methyl-2-propenyl 5R,6S-6-(1-R-hydroxyethyl)-2-(1R-oxo-3S-thiolanylthio)-2-penem-3-carboxylate:

A solution of sodium p-toluenesulfinate tetrahydrate (151 mg, 0.604 mmol) in methanol (2.3 ml) was added at room temperature to a suspension of 2-methyl-2-propenyl 5R,6S-6-(1R-hydroxyethyl)-2-(1R-oxo-3S-thiolanylthio)-2-penem-3-carboxylate (244 mg, 0.604 mmol) prepared in Preparation 1 and tetrakis(triphenylphosphine)palladium (48.6 mg, 42.1 μmol) in tetrahydrofuran (3.8 ml). The reaction mixture was stirred at room temperature for 130 minutes and ethyl acetate (12 ml) was added dropwise to precipitate the sodium salt of the target compound. Celite (0.8 g) was added to the mixture. After filtration, the precipitates and celite were washed three times with ethyl acetate (3 ml) and the precipitates were dissolved in water (5 ml+2 ml×3). The aqueous solution was acidified with an ion-exchange resin (Manufactured by Mitsubishi Chem. under the trade name of DIAION PK216H) and acetone (7.5 ml) was added. The resin was filtered off and washed three times with acetone-water (2:1,2 ml×3). The combined filtrates were concentrated at 24° C. by an evaporator to strip acetone and freeze-dried to give light yellow powders (198 mg) in 94% yield.

Comparative Example 2

Removal of 2-Methyl-2-Propenyl From 2-methyl-2-propenyl 5R,6S-6-(1R-hydroxyethyl)-2-(1R-oxo-3S-thiolanylthio)-2-penem-3-carboxylate:

Triphenylphosphine (196 mg, 0.746 mmol), sodium 2-ethylhexanoate (993 mg, 5.98 mmol) and 2-methyl-2-propenyl 5R,6S-6-(1R-hydroxyethyl)-2-(1R-oxo-3S-thiolanilthio)-2-penem-3-carboxylate prepared in Preparation 1 (2.00 g, 4.98 mmol) were suspended in methylene chloride (46 ml) to which was subsequently added tetrakis(triphenylphosphine)palladium (325 mg, 281 μmol). The palladium catalyst was supplemented (79.9 mg, 69 μmol after 30 minutes; 40.3 mg, 35 μmol after 90 minutes). After stirring the reaction mixture for 2 hours at room temperature, extraction was carried out by adding water (10 ml), followed by one more extraction with water (2.6 ml). The water layers were combined, treated with activated carbon (0.17 g) and then filtered. The remaining filter cake was washed with water (0.8 ml). The water layers were again combined, treated with activated carbon (0.17 g) and then filtered. The remaining filter cake was washed with water (0.8 ml). The thus combined aqueous solution was cooled to 5° C., acidified to pH 2.5 by adding concentrated hydrochloric acid and then stirred at 5° C. for 30 minutes. The precipitate thus formed was filtered, washed 4 times with water (1 ml) and then dried in vacuo to obtain 5R,6S-6-(1R-hydroxyethyl)-2-(1R-oxo-3S-thiolanylthio)-2-penem-3-carboxylic acid as a off-white powder (897 mg) with a yield of 52%.

In view of the results of Example 3 and Comparative Example 2, it was found that the process of the present invention can improve the product yield considerably in comparison with the prior art process even when other allyl compound is treated.

Example 4

Removal of 2-Butenyl From 2-Butenyl 5R,6S-6-(1-R-Hydroxyethyl)-2-(1R-oxo-3S-thiolanylthio)-2-penem-3-carboxylate:

A solution of sodium p-toluenesulfinate tetrahydrate (155 mg, 0.618 mmol) in methanol (2.1 ml) was added at room temperature to a suspension of 2-butenyl 5R,6S-6-(1R-hydroxyethyl)-2-(1R-oxo-3S-thiolanylthio)-2-penem-3-carboxylate (227 mg, 0.562 mmol) prepared in Preparation 3 and tetrakis(triphenylphosphine)palladium (28.0 mg, 24.2 μmol) in tetrahydrofuran (3.5 ml). The reaction mixture was stirred at room temperature for 35 minutes and ethyl acetate (11 ml) was added dropwise to precipitate the sodium salt of the target compound. Celite (0.8 g) was added to the mixture. After filtration, the precipitates and celite were washed three times with ethyl acetate (3 ml) and dissolved in water (5 ml+2 ml×3). The aqueous solution was acidified with an ion-exchange resin (Manufactured by Mitsubishi Chem. under the trade name of DIAION PK216H) and acetone (7.5 ml) was added. The resin was filtered off and washed three times with acetone-water (2:1, 1.5 ml×3). The combined filtrates were concentrated at 20° C. by an evaporator to strip acetone and freeze-dried to give light yellow powders (178 mg) in 91% yield.

Example 5

Removal of Cinnamyl From Cinnamyl 5R,6S-6-(1R-Hydroxyethyl)-2-(1R-oxo-3S-thiolanyl-thio)-2-penem-3-carboxylate:

A solution of sodium p-toluenesulfinate tetrahydrate (149 mg, 0.594 mmol) in methanol (2.3 ml) was added at room temperature to a suspension of cinnamyl 5R,6S-6-(1R-hydroxyethyl)-2-(1R-oxo-3S-thiolanylthio)-2-penem-3-carboxylate (251 mg, 0.540 mmol) prepared in Preparation 4 and tetrakis(triphenylphosphine)palladium (31.2 mg, 27.0 μmol) in tetrahydrofuran (3.4 ml). The reaction mixture was stirred at room temperature for 30 minutes and ethyl acetate (11 ml) was added dropwise to precipitate the sodium salt of the target compound. Celite (0.8 g) was added to the mixture. After filtration, the precipitates and celite were washed three times with ethyl acetate (3 ml) and the precipitates were dissolved in water (5 ml+2 ml×3). The aqueous solution was acidified with an ion-exchange resin (Manufactured by Mitsubishi Chem. under the trade name of DIAION PK216H) and acetone (7.5 ml) was added. The resin was filtered off and washed three times with acetone-water (2:1, 2 ml×3). The combined filtrates were concentrated at 20° C. by an evaporator to strip acetone and freeze-dried to give light yellow powders (177 mg)in 94% yield.

Example 6

Removal of Propenyl From Propenyl 5R,6S-6-(1R-Hydroxyethyl)-2-(1R-oxo-3S-thiolanylthio)-2-penem-3-carboxylate:

A solution of sodium p-toluenesulfinate tetrahydrate (1.06 g, 4.23 mmol) in water (7 ml) was added at room temperature to a suspension of 2-propenyl 5R,6S-6-(1R-hydroxyethyl)-2-(1R-oxo-3S-thiolanylthio)-2-penem-3-carboxylate (1.54 g, 3.95 mmol) prepared in Preparation 2 and tetrakis(triphenylphosphine)palladium (209 mg, 0.180 mmol) in tetrahydrofuran (20 ml). The reaction mixture was stirred at room temperature for 25 minutes. After partition of diethyl ether (20 ml), the ether layer was extracted with water (1 ml). The water extract was treated with active charcoal (0.28 g) and filtered. The filter cake was rinsed with water (1.5 ml). The combined aqueous solution was cooled to 5° C., acidified to a pH of 2.5 by adding conc. hydrochloric acid and stirred at 5° C. for 3 min. The precipitates of 5R,6S-6-(1R-hydroxyethyl)-2-(1R-oxo-3S-thiolanylthio)-2-penem-3-carboxylic acid were filtered off, washed with water (1 ml) and dried in vacuum to give pale pink powders (1.20 g) in 87% yield.

Example 7

Removal of 2-Chloro-2-Propenyl From 2-Chloro-2-Propenyl 5R,6S-6-(1R-Hydroxyethyl)-2-(1R-oxo-3S-thiolanylthio)-2-penem-3-carboxylate:

Tetrahydrofuran (3.37 ml) and water (1.35 ml) were added at room temperature to a mixture of sodium p-carboxybenzenesulfinate hydrate (118 mg), 2-chloro-2-propenyl 5R,6S-6-(1R-hydroxyethyl)-2-(1R-oxo-3S-thiolanylthio)-2-penem-3-carboxylate (200 mg, 0.471 mmol) prepared in Preparation 1 and tetrakis(triphenylphosphine)palladium (28.7 mg, 24.8 μmol). The reaction mixture was stirred at room temperature for 90 minutes. After addition of water (1 ml) the mixture was extracted three times with diethyl ether (9 ml+4.5 ml×2). The aqueous layer was cooled to 5° C., acidified to a pH of 2.5 by adding conc. hydrochloric acid and stirred at 5° C. for 30 min. The precipitates were filtered off, washed three times with water (1 ml×3) and dried in vacuum to give a mixture (246 mg, off-white powders) of 5R,6S-6-(1R-hydroxyethyl)-2-(1R-oxo-3S-thiolanylthio)-2-penem-3-carboxylicacid and 2-chloro-2-propenyl p-carboxyphenyl sulfone in a molecular ratio of 4:3.

Example 8

Removal of 2-Chloro-2-Propenyl From 2-Chloro-2-Propenyl 5R,6S-6-(1R-Hydroxyethyl)-2-(1R-oxo-3S-thiolanylthio)-2-penem-3-carboxylate:

A solution of sodium octylsulfinate (98.8 mg, 0.492 mmol) in methanol (1.6 ml) was added at room temperature to a suspension of 2-chloro-2-propenyl 5R,6S-6-(1R-hydroxyethyl)-2-(1R-oxo-3S-thiolanylthio)-2-penem-3-carboxylate (200 mg, 0.470 mmol) prepared in Preparation 1 and tetrakis(triphenylphosphine)palladium (29.9 mg, 25.9 μmol) in tetrahydrofuran (3.2 ml). The reaction mixture was stirred at room temperature for 6.5 hours and ethyl acetate (8 ml) was added dropwise to precipitate the sodium salt of the target compound. Celite (0.4 g) was added to the mixture. After filtration, the precipitates and celite were washed twice with ethyl acetate (2 ml×2) and the precipitates were dissolved twice in water (2 ml+1 ml). The aqueous solution was acidified with ion-exchange resin (DIAION PK216H) and acetone (5 ml) was added. The resin was filtered off and washed with acetone-water (5:1,1 ml). The combined filtrates were concentrated at 20° C. by an evaporator to strip acetone and freeze-dried to give light yellow powders (135 mg) in 82% yield.

Example 9

Removal of 2-Chloro-2-Propenyl From 2-Chloro-2-Propenyl 5R,6S-6-(1R-Hydroxyethyl)-2-(1R-oxo-3S-thiolanylthio)-2-penem-3-carboxylate:

A solution of sodium ethylsulfinate (57.3 mg, 0.493 mmol) in methanol (1.6 ml) was added at room temperature to a suspension of 2-chloro-2-propenyl 5R,6S-6-(1R-hydroxyethyl)-2-(1R-oxo-3S-thiolanylthio)-2-penem-3-carboxylate (200 mg, 0.470 mmol) prepared in Preparation 1 and tetrakis(triphenylphosphine)palladium (28.9 mg, 25.0 μmol) in tetrahydrofuran (3.2 ml). The reaction mixture was stirred at room temperature for 6.5 hours and ethyl acetate (8 ml) was added dropwise to precipitate the sodium salt of the target compound. Celite (0.45 g) was added to the mixture. After filtration, the precipitates and celite were washed twice with ethyl acetate (2 ml×2) and the precipitates were dissolved twice in water (2 ml+1 ml). The aqueous solution was acidified with ion-exchange resin (DIAION PK216H) and acetone (5 ml) was added. The resin was filtered off and washed with acetone-water (2:1, 1 ml). The combined filtrates were concentrated at 20° C. by an evaporator to strip acetone and freeze-dried to give light yellow powders (149 mg) in 91% yield.

Example 10

Removal of 2-Chloro-2-Propenyl From 2-Chloro-2-Propenyl 5R,6S-6-(1R-Hydroxyethyl)-2-(1R-oxo-3S-thiolanylthio)-2-penem-3-carboxylate:

2-Chloro-2-propenyl 5R,6S-6-(1R-hydroxyethyl)-2-(1R-oxo-3S-thiolanylthio)-2-penem-3-carboxylate (7.82 g, 18.4 mmol) prepared in Preparation 1, triphenylphosphine (723 mg, 2.76 mmol) and tetrakis(triphenylphosphine)palladium (1.06 g, 0.92 mmol) were suspended in methylene chloride (196 ml) and benzenesulfinic acid (2.87 g, 20.2 mmol) to which was subsequently added at room temperature. After the reaction mixture was stirred for 1 hour at room temperature, and the crystals of interest formed in the reaction solution were collected by filtration, washed 3 times with methylene chloride (7 ml) and then dried in vacuo. White powder (6.19 g) was obtained with a yield of 96%.

Comparative Example 3

2-Chloro-2-propenyl 5R,6S-6-(1R-hydroxyethyl)-2-(1R-oxo-3S-thiolanilthio)-2-penem-3-carboxylate (16.9 g, 39.9 mmol), triphenylphosphine (1.46 g, 5.57 mmol) and sodium 2-ethylhexanoate (8.08 g, 48.6 mmol) were suspended in methylene chloride (365 ml). Tetrakis(triphenylphosphine)palladium (2.48 g, 2.14 mmol) was added to the suspension at 20° C. After 2 hours of stirring at 20° C., the resulting brown reaction solution was cooled to 0° to 5° C. and extracted by adding water (86.5 ml). Extraction with water (22 ml) was repeated again. The water extracts were combined, cooled to 0° to 5° C. and adjusted to pH 5.2 with concentrated hydrochloric acid. This was treated with activated carbon (1.46 g), and filtrated. The resulting filter cake was washed with water (6.7 ml). Similar treatment with activated carbon was repeated again. The filtrates and washing solutions were combined, cooled to 5° C., adjusted to pH 2.5 with concentrated hydrochloric acid and then stirred at 5° C. for 1 hour. The resulting precipitate was collected by filtration, washed 5 times with water (8 ml) and twice with acetone (6.6 ml) and then dried under a reduced pressure at room temperature. Off-white powder (10.6 g) was obtained with a yield of 76%.

Comparative Example 5

The procedure of Example 10 was repeated except that the following reactant, catalyst and solvent were used.

dimedone 16.5 mg (0.118 mmol)

2-chloro-2-propenyl5R,6S-6-(1R-hydroxyethyl)-2-(1R-oxo-3S-thiolanylthio)-2-penem-3-carboxylate 50 mg (0.118 mmol)

tetrakis(triphenylphosphine)palladium 5.1 mg (4.4 μmol)

triphenylphosphine 9.9 mg (70 μmol)

tetrahydrofuran 5 ml

As the results, the compound of interest was not obtained.

In view of the results of Example 10 and Comparative Examples 4 and 5, it was found that the process of the present invention can improve the product yield considerably in comparison with the prior art process.

Example 11

Removal of 2-chloro-2-propenyl group From 2-chloro-2-propenyl 5R,6S-6-(1R-hydroxyethyl)-2-(1R-oxo-3S-thiolanilthio)-2-penem-3-carboxylate using sodium benzenesulfinate Methanol solution (1.6 ml) of sodium benzenesulfinate (99.0 mg, 0.494 mmol) was added at room temperature to a suspension of tetrahydrofuran (3.2 ml) containing 2-chloro-2-propenyl 5R,6S-6-(1R-hydroxyethyl)-2-(1R-oxo-3S-thiolanylthio)-2-penem-3-carboxylate (203 mg, 0.479 mmol) prepared in Preparation 1 and tetrakis(triphenylphosphine)palladium (32.6 mg, 28.3 μmol). After stirring the reaction mixture for 3.6 hours at room temperature, the palladium catalyst (10 mg, 8.7 μmol) was again added. After 6.5 hours, ethyl acetate (8 ml) was added dropwise, thereby effecting precipitation of sodium salt of the compound of interest. Celite (0.6 g) was added to the mixture thus obtained. After filtration, the precipitate and celite were washed twice with ethyl acetate (2 ml). The precipitate was dissolved in water (2 ml) and washed with acetone/water (1:1, 3 ml). The aqueous solution thus obtained was acidified with an ion exchange resin (manufactured by Mitsubishi Chemical Industries, Ltd.; trade name, DIAION PK216H) and mixed with acetone (5 ml). The ion exchange resin was separated by filtration and washed with acetone/water (2:1, 1 ml). The filtrates were combined, concentrated by evaporating acetone at 20° C. using an evaporator and then freeze-dried to obtain a light brown powder (157 mg) with a yield of 94%.

Example 12

Removal of 2-chloro-2-propenyl group From 2-chloro-2-propenyl 5R,6S-6-(1R-hydroxyethyl)-2-(1R-oxo-3S-thiolanylthio)-2-penem-3-carboxylate using lithium p-toluenesulfinate:

Lithium p-toluenesulfinate (64.6 mg, 0.398 mmol) was added at room temperature to a solution of tetrahydrofuran-methanol (5:3, 3.3 ml) containing 2-chloro-2-propenyl5R,6S-6-(1R-hydroxyethyl)-2-(1R-oxo-3S-thiolanilthio)-2-penem-3-carboxylate (140 mg, 0.330 mmol) prepared in Preparation 1 and tetrakis(triphenylphosphine)palladium (27.4 mg, 23.7 μmol). After stirring the reaction mixture for 60 minutes at room temperature, ethyl acetate (6.6 ml) was added dropwise, thereby effecting precipitation of sodium salt of the compound of interest. Celite (0.6 g) was added to the mixture thus obtained. After filtration, the precipitate and celite were washed 3 times with ethyl acetate (1.5 ml). The precipitate was dissolved in water (2 ml) and washed 3 times with water (1 ml). The aqueous solution thus obtained was acidified with an ion exchange resin (manufactured by Mitsubishi Chemical Industries, Ltd.; trade name, DIAION PK216H) and mixed with acetone (5 ml). The ion exchange resin was separated by filtration and washed 3 times with acetone/water (2:1, 1 ml). The filtrates were combined, concentrated by evaporating acetone at 20° C. using an evaporator and then freeze-dried to obtain a light yellow powder (109 mg) with a yield of 94%.

Example 13

Removal 2-chloro-2-propenyl group From 2-chloro-2-propenyl 5R,6S-6-(1R-hydroxyethyl)-2-(1R-oxo-3S-thiolanylthio)-2-penem-3-carboxylateusingsodium4-chloro-3-nitrobenzenesulfinate:

Tetrahydrofuran-methanol (5:3, 3.9 ml) was added at room temperature to a mixture of 2-chloro-2-propenyl5R,6S-6-(1R-hydroxyethyl)-2-(1R-oxo-3S-thiolanylthio)-2-penem-3-carboxylate (165 mg, 0.389 mmol) prepared in Preparation 1, sodium 4-chloro-3-nitrobenzenesulfinate (106 mg, 0.433 mmol), tetrakis(triphenylphosphine)palladium (29.5 mg, 25.5 mmol) and triphenylphosphine (29.7 mg, 0.113 μmol). After stirring the reaction mixture for 130 minutes at room temperature, ethyl acetate (8 ml) was added dropwise, thereby effecting precipitation of sodium salt of the compound of interest. Celite (0.6 g) was added to the thus obtained mixture. After filtration, the precipitate and celite were washed 3 times with ethyl acetate (2 ml). The precipitate was dissolved in water (1.5 ml) and washed 3 times with water (1.0 ml). The aqueous solution thus obtained was acidified with an ion exchange resin (manufactured by Mitsubishi Chemical Industries, Ltd.; trade name, DIAION PK216H) and mixed with acetone (6 ml). The ion exchange resin was separated by filtration and washed 3 times with acetone/water (2:1, 1.0 ml). The filtrates were combined, concentrated by evaporating acetone at 21° C. using an evaporator and then freeze-dried to obtain a light yellow powder (98.2 mg) with a yield of 72%.

Example 14

Removal of 2-chloro-2-propenyl group From 2-chloro-2-propenyl 5R,6S-6-(1R-hydroxyethyl)-2-(1R-oxo-3S-thiolanylthio)-2-penem-3-carboxylate using sodium 4-acetamidobenzenesulfinate:

Tetrahydrofuran (3.3 ml) and methanol (2.0 ml) were added at room temperature to a mixture consisting of sodium 4-acetamidobenzenesulfinate (139 mg, 0.626 mmol), 2-chloro-2-propenyl 5R,6S-6-(1R-hydroxyethyl)-2-(1R-oxo-3S-thiolanylthio)-2-penem-3-carboxylate (226 mg, 0.534 mmol) prepared in Preparation 1 and tetrakis(triphenylphosphine)palladium (35.5 mg, 30.7 μmol). After stirring the reaction mixture for 60 minutes at room temperature, ethyl acetate (11 ml) was added dropwise, thereby effecting precipitation of sodium salt of the compound of interest. Celite (0.8 g) was added to the mixture thus obtained. After filtration, the precipitate and celite were washed 3 times with ethyl acetate (1.5 ml). The precipitate was dissolved in water (3 ml) and washed 3 times with water (1.5 ml). The aqueous solution thus obtained was acidified with an ion exchange resin (manufactured by Mitsubishi Chemical Industries, Ltd.; trade name, DIAION PK216H) and mixed with acetone (7.5 ml). The ion exchange resin was separated by filtration and washed 3 times with acetone/water (2:1, 1.5 ml). The filtrates were combined, concentrated by evaporating acetone at 19° C. using an evaporator and then freeze-dried to obtain a light yellow powder (176 mg) with a yield of 94%.

Example 15

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate using sodium thiophene-2-sulfinate:

Tetrahydrofuran-methanol (5:3, 2.0 ml) was added at room temperature to a mixture of 2-chloro-2-propenyl 5R,6S-6-(1R-hydroxyethyl)-2-(1R-oxo-3S-thiolanylthio)-2-penem-3-carboxylate (85.4 mg, 0.201 mmol) prepared in Preparation 1, sodium thiophene-2-sulfinate (40.1 mg, 0.236 mmol) and tetrakis(triphenylphosphine)palladium (16.9 mg, 14.6 mmol). After stirring the reaction mixture for 150 minutes at room temperature, ethyl acetate (4 ml) was added dropwise, thereby effecting precipitation of sodium salt of the compound of interest. Celite (0.4 g) was added to the mixture thus obtained. After filtration, the precipitate and celite were washed 3 times with ethyl acetate (1 ml), and the precipitate was dissolved in water (1.0 ml) and washed 3 times with water (1.0 ml). The thus obtained aqueous solution was acidified with an ion exchange resin (manufactured by Mitsubishi Chemical Industries, Ltd.; trade name, DIAION PK216H) and mixed with acetone (3 ml). The ion exchange resin was separated by filtration and washed 3 times with acetone/water (2:1, 1.0 ml). The filtrates were combined, concentrated by evaporating acetone at 21° C. using an evaporator and then freeze-dried to obtain a light yellow powder (67.6 mg) with a yield of 96%.

Example 16

Removal of 2-chloro-2-propenyl group from 2-chloro-2-propenyl5R,6S-6-(1R-hydroxyethyl)-2-(1R-oxo-3S-thiolanylthio)-2-penem-3-carboxylate using sodium methylsulfinate:

Tetrahydrofuran (3.2 ml) was added at room temperature to a mixture consisting of tetrakis(triphenylphosphine)palladium (32.6 mg, 28.3 μmol) and 2-chloro-2-propenyl 5R,6S-6-(1R-hydroxyethyl)-2-(1R-oxo-3S-thiolanylthio)-2-penem-3-carboxylate (200 mg, 0.471 mmol) prepared in Preparation 1. To this was added sodium methylsulfinate (50.5 mg, 0.494 mmol) which has been dissolved in methanol (1.6 ml). After stirring the reaction mixture for 2 hours at room temperature, ethyl acetate (8 ml) was added dropwise, thereby effecting precipitation of sodium salt of the compound of interest. Celite (0.6 g) was added to the mixture thus obtained. After filtration, the precipitate and celite were washed twice with ethyl acetate (2 ml). The precipitate was dissolved in water (2 ml) and washed with water (1 ml). The aqueous solution thus obtained was acidified with an ion exchange resin (manufactured by Mitsubishi Chemical Industries, Ltd.; trade name, DIAION PK216H) and mixed with acetone (5 ml). The ion exchange resin was separated by filtration and washed 3 times with acetone/water (5:1, 2 ml). The filtrates were combined, concentrated by evaporating acetone using an evaporator and then freeze-dried to obtain a light brown powder (141 mg) with a yield of 86%.

Example 17

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate using sodium isobutylsulfinate:

Methanol solution (1.6 ml) of sodium isobutylsulfinate (71.3 mg, 0.494 mmol) was added at room temperature to a suspension of tetrahydrofuran (3.2 ml) containing 2-chloro-2-propenyl 5R,6S-6-(1R-hydroxyethyl)-2-(1R-oxo-3S-thiolanylthio)-2-penem-3-carboxylate (200 mg, 0.471 mmol) prepared in Preparation 1 and tetrakis(triphenylphosphine)palladium (32.6 mg, 28.3 μmol). The reaction mixture was stirred for 6.3 hours at room temperature. To this was added ethyl acetate (8 ml) dropwise to effect precipitation of sodium salt of the compound of interest. Celite (0.6 g) was added to the mixture thus obtained. After filtration, the precipitate and celite were washed twice with ethyl acetate (2 ml), and the precipitate was dissolved in water (2 ml) and washed with water (1 ml). The thus obtained aqueous solution was acidified with an ion exchange resin (manufactured by Mitsubishi Chemical Industries, Ltd.; trade name, DIAION PK216H) and mixed with acetone (5 ml). The ion exchange resin was separated by filtration and washed with acetone/water (5: 1, 1 ml). The filtrates were combined, concentrated by evaporating acetone at 20° C. using an evaporator and then freeze-dried to obtain a light brown powder (148 mg) with a yield of 90%.

Example 18

Removal of 2-chloro-2-propenyl group from 2-chloro-2-propenyl 5R,6S-6-(1R-hydroxyethyl)-2-(1R-oxo-3S-thiolanilthio)-2-penem-3-carboxylate using sodium hexadecylsulfinate:

Tetrahydrofuran (3.5 ml) and methanol (2.5 ml) were added to a mixture consisting of sodium hexadecylsulfinate (176 mg, 0.564 mmol), 2-chloro-2-propenyl 5R,6S-6-(1R-hydroxyethyl)-2-(1R-oxo-3S-thiolanilthio)-2-penem-3-carboxylate(219 mg, 0.516 mmol) prepared in Preparation 1 and tetrakis(triphenylphosphine)palladium (38.0 mg, 33 mmol). The reaction mixture was stirred for 6.4 hours at room temperature. To this was added ethyl acetate (10 ml) dropwise, thereby effecting precipitation of sodium salt of the compound of interest. Celite (0.7 g) was added to the mixture thus obtained. After filtration, the precipitate and celite were washed twice with ethyl acetate (2 ml), and the precipitate was dissolved in water (2 ml) and washed with water (1 ml). The aqueous solution thus obtained was acidified with an ion exchange resin (manufactured by Mitsubishi Chemical Industries, Ltd.; trade name, DIAION PK216H) and mixed with acetone (5 ml). The ion exchange resin was separated by filtration and washed with acetone/water (5:1, 2 ml). The filtrates were combined, concentrated by evaporating acetone at 20° C. using an evaporator and then freeze-dried to obtain a light yellow powder (144 mg) with a yield of 80%.

Example 19

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate using Sodium hydroxymethanesulfinate:

Sodium hydroxymethanesulfinate (61.9 mg, 0.402 mmol) was added at room temperature to a solution of tetrahydrofuran-methanol (5:3, 3.3 ml) containing 2-chloro-2-propenyl 5R,6S-6-(1R-hydroxyethyl)-2-(1R-oxo-3S-thiolanilthio)-2-penem-3-carboxylate (142 mg, 0.335 mmol) prepared in Preparation 1 and tetrakis(triphenylphosphine)palladium (24.3 mg, 21.0 μmol). After stirring the reaction mixture for 80 minutes at room temperature, ethyl acetate (6.6 ml) was added dropwise, thereby effecting precipitation of sodium salt of the compound of interest. Celite (0.6 g) was added to the mixture thus obtained. After filtration, the precipitate and celite were washed 3 times with ethyl acetate (1.5 ml). The precipitate was dissolved in water (2 ml) and washed 3 times with water (1 ml). The aqueous solution thus obtained was acidified with an ion exchange resin (manufactured by Mitsubishi Chemical Industries, Ltd.; trade name, DIAION PK216H) and mixed with acetone (5 ml). The ion exchange resin was separated by filtration and washed 3 times with acetone/water (2:1, 1 ml). The filtrates were combined, concentrated by evaporating acetone at 20° C. using an evaporator and then freeze-dried to obtain a light yellow powder (94.5 mg) with a yield of 86%.

Example 20

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate using ammonium p-toluenesulfinate:

P-Toluenesulfinic acid (53.1 mg, 0.340 mmol) was dissolved in chloroform (1 ml) and 25% aqueous ammonia (0.5 ml) was added to the solution at room temperature and stirred vigorously, the resulting mixture was concentrated under a reduced pressure to obtain a white solid. At room temperature, this was mixed with 2-chloro-2-propenyl 5R,6S-6-(1R-hydroxyethyl)-2-(1R-oxo-3S-thiolanylthio)-2-penem-3-carboxylate (132 mg, 0.311 mmol) prepared in Preparation 1 and dissolved in methylene chloride (3.1 ml). To this was added tetrakis(triphenylphosphine)palladium (25.0 mg, 22 μmol) at room temperature. The reaction mixture was stirred for 3 hours at room temperature, extracted by adding water (1 ml) and then extracted twice with water (1.5 ml). The water extracts were combined, treated with activated carbon and filtered, and the resulting filtrate was adjusted to pH 2 with concentrated hydrochloric acid. The precipitate thus formed was filtered, washed twice with water (0.5 ml) and then dried in vacuo at room temperature. A white powder (51.9 mg) was obtained with a yield of 48%.

Example 21

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate using triethylammonium p-toluenesulfinate:

2-Chloro-2-propenyl 5R,6S-6-(1R-oxo-3S-thiolanylthio)-2-penem-3-carboxylate (77.5 mg, 0.183 mmol) prepared in Preparation 1, p-toluenesulfinic acid (32.4 mg, 0.207 mmol) and triethylamine (21.0 mg, 0.207 mmol) were dissolved in methylene chloride (1.8 ml) to which was subsequently added tetrakis(triphenylphosphine)palladium (14.5 mg, 12.5 μmol) at room temperature. The reaction mixture was stirred for 30 minutes at room temperature, extracted by adding water (1.8 ml) and then extracted twice with water (0.9 ml). The water extracts were combined, treated with activated carbon and then filtered. The resulting filtrate was adjusted to pH 2 with concentrated hydrochloric acid. The precipitate thus formed was collected by filtration, washed twice with water (0.5 ml) and then dried in vacuo at room temperature. A light off-white powder (32.4 mg) was obtained with a yield of 51%.

Example 22

Removal of 2-chloro-2-propenyl group from 2-chloro-2-propenyl 5R,6S-6-(1R-hydroxyethyl)-2-(1R-oxo-3S-thiolanilthio)-2-penem-3-carboxylate using tetrabutylammonium benzenesulfinate:

Methylene chloride (7.0 ml) was added at room temperature to a mixture consisting of tetrabutylammonium benzenesulfinate (300 mg, 0.81 mmol), 2-chloro-2-propenyl 5R,6S-6-(1R-hydroxyethyl)-2-(1R-oxo-3S-thiolanilthio)-2-penem-3-carboxylate (300 mg, 0.707 mmol) prepared in Preparation 1 and tetrakis (triphenylphosphine)palladium (49 mg, 42.4 μmol). The reaction mixture was stirred for 25 minutes at room temperature, extracted by adding water (1.5 ml) and then extracted twice (1 ml×2). The water layers were combined, cooled to 5° C., acidified to pH 2.5 by adding aqueous 1N hydrochloric acid and then stirred at 5° C. for 30 minutes. The precipitate thus formed was collected by filtration, washed with cool water (2 ml) and then dried in vacuo. A white powder (173 mg) was obtained with a yield of 70%.

Example 23

Removal of 2-chloro-2-propenyl group from 2-chloro-2-propenyl (2S,5R)-3,3-dimethyl-4,4,7-trioxo-4-thia(VI)-1-azabicyclo[3.2.0]heptane-2-carboxylate:

Tetrahydrofuran-methanol (5:3, 10.5 ml) was added at room temperature to a mixture of 2-chloro-2-propenyl (2S, 5R)-3,3-dimethyl-4,4,7-trioxo-4-thia(VI)-1-azabicyclo [3.2.0]heptane-2-carboxylate (323 mg, 1.05 mmol) prepared in Preparation 5, sodium p-toluenesulfinate (289 mg, 1.15 mmol) and tetrakis(triphenylphosphine)palladium (68.0 mg, 58.8 μmol). The reaction mixture was stirred for 60 minutes at room temperature. Sodium salt of the compound of interest was precipitated. To this were added ethyl acetate (21 ml) and celite (2 g). After filtration, the precipitate and celite were washed 3 times with ethyl acetate (4 ml). The precipitate was dissolved in water (5 ml) and washed 3 times with water (2.0 ml). The aqueous solution thus obtained was acidified with an ion exchange resin (manufactured by Mitsubishi Chemical Industries, Ltd.; trade name, DIAION PK216H). The ion exchange resin was separated by filtration and washed 3 times with acetone/water (2: 1, 3 ml). The filtrates were combined and concentrated by evaporating acetone at 21° C. using an evaporator. This was further freeze-dried to obtain a white powder (242 mg) with a yield of 99%.

Example 24

Removal of 2-propenyl group from 2-propenyl 7-benzamido-3-acetoxymethyl-3-cepham-4-carboxylate;

Methanol solution (3.0 ml) of sodium p-toluenesulfinate (218 mg, 0.871 mmol) was added at room temperature to a solution of tetrahydrofuran (5.0 ml) containing 2-propenyl 7-benzamido-3-acetoxymethyl-3-cepham-4-carboxylate (330 mg, 0.792 mmol) prepared in Preparation 6 and tetrakis(triphenylphosphine)palladium (54.9 mg, 47.5 μmol). The reaction mixture was stirred for 60 minutes at room temperature. Sodium salt of the compound of interest was precipitated. This was mixed with ethyl acetate (16 ml) and stirred for 30 minutes. The precipitate thus formed was collected by filtration, washed 3 times with ethyl acetate (2 ml), dried in vacuo at room temperature to obtain the sodium salt of 7-benzamido-3-acetoxymethyl-3-cepham-4-carboxylic acid (253 mg) as a white powder with a yield of 80%.

Example 25

Removal of allyloxycarbonyl group from allyl N-(p-methoxyphenyl)carbamate:

Tetrakis(triphenylphosphine)palladium (30.3 mg, 26.2 μmol) was added to a methylene chloride solution (3.7 ml) of p-toluenesulfinic acid (64.3 mg, 0.411 mmol) and allyl N-(p-methoxyphenyl)carbamate (77.6 mg, 0.374 mmol) prepared in Preparation 7. The reaction mixture was stirred for 40 minutes at room temperature. The reaction solution was subjected to a silica gel chromatography to obtain p-anisidine (36.3 mg) with a yield of 79%.

Example 26

Removal of allyloxycarbonyl group from 3-O-allyloxycarbonyl-1,2:5,6-di-O-isopropylidene-α-D-glucofuranose:

Toluenesulfinic acid (59.3 mg, 0.380 mmol) was added to a methylene chloride solution (3.3 ml) of 3-O-allyloxycarbonyl-1,2: 5,6-di-O-isopropylidene-α-D-glucofuranose (115 mg, 0.334 mmol) prepared in Preparation 8 and tetrakis(triphenylphosphine)palladium (27.0 mg, 23.4 αmol). The reaction mixture was stirred for 30 minutes at room temperature, mixed with triethylamine (6.8 mg, 67 mmol) and then subjected to a silica gel chromatography to obtain 1,2:5,6-di-O-isopropylidene-a-D-glucofuranose (85.6 mg) as a white solid with a yield of 98%.

Example 27

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate:

Palladium diacetate (20.5 mg, 91.3 mmol) was added at room temperature to a solution of tetrahydrofuran-methanol (5:3, 4.5 ml) containing 2-chloro-2-propenyl 5R,6S-6-(1R-hydroxyethyl)-2-(1R-oxo-3S-thiolanylthio)-2-penem-3-carboxylate (182 mg, 0.430 mmol) prepared in Preparation 1, sodium p-toluenesulfinate (126 mg, 0.502 mmol) and triethyl phosphite (52.6 mg, 0.317 mmol). After stirring the reaction mixture for 80 minutes at room temperature, ethyl acetate (9 ml) was added dropwise, thereby effecting precipitation of sodium salt of the compound of interest. Celite (0.7 g) was added to the mixture thus obtained. After filtration, the precipitate and celite were washed 3 times with ethyl acetate (2 ml), and the precipitate was dissolved in water (2.5 ml) and washed 3 times with water (1.5 ml). The aqueous solution thus obtained was acidified with an ion exchange resin (manufactured by Mitsubishi Chemical Industries, Ltd.; trade name, DIAION PK216H) and mixed with acetone (6 ml). The ion exchange resin was separated by filtration and washed 3 times with acetone/water (2:1, 1.5 ml). The filtrates were combined, concentrated by evaporating acetone at 20° C. using an evaporator and then freeze-dried to obtain a light yellow powder (121 mg) with a yield of 80%.

Comparative Example 6

Palladium diacetate (20.8 mg, 92.6 μmol) was added at room temperature to a solution of tetrahydrofuran-methanol (5:3, 4.5 ml) containing 2-chloro-2-propenyl 5R,6S-6-(1R-hydroxyethyl)-2-(1R-oxo-3S-thiolanylthio)-2-penem-3-carboxylate prepared in Preparation 1 (191 mg, 0.451 mmol), sodium 2-ethylhexanoate (105 mg, 0.630 mmol) and triethyl phosphite (52.4 mg, 0.316 mmol). After stirring the reaction mixture for 6 hours at room temperature, ethyl acetate (9 ml) was added dropwise, thereby effecting precipitation of sodium salt of the compound of interest. Celite (0.7 g) was added to the mixture thus obtained. After filtration, the precipitate and celite were washed 3 times with ethyl acetate (2 ml). The precipitate was dissolved in water (2.5 ml) and washed 3 times with water (1.5 ml). The aqueous solution thus obtained was acidified with an ion exchange resin (manufactured by Mitsubishi Chemical Industries, Ltd.; trade name, DIAION PK216H) and mixed with acetone (6 ml). The ion exchange resin was separated by filtration and washed 3 times with acetone/water (2:1, 1.5 ml). The filtrates were combined, concentrated by evaporating acetone at 20° C. using an evaporator and then freeze-dried to obtain a light yellow powder (67.9 mg) with a yield of 45%.

In view of the results of Example 27 and Comparative Example 6, it was found that the process of the present invention can improve the product yield considerably in comparison with the prior art process even when other palladium catalyst is used for the treatment.

Example 28

Removal of 2-chloro-2-propenyl group from 2-chloro-2-propenyl 5R,6S-6-(1R-hydroxyethyl)-2-(1R-oxo-3S-thiolanylthio)-2-penem-3-carboxylate:

Tetrahydrofuran-methanol (5:3, 5.6 ml) and triethyl phosphite (38.3 mg, 0.230 mmol) were added at room temperature to a mixture consisting of 2-chloro-2-propenyl 5R,6S-6-(1R-hydroxyethyl)-2-(1R-oxo-3S-thiolanylthio)-2-penem-3-carboxylate (237 mg, 0.558 mmol) prepared in Preparation 1, sodium p-toluenesulfinate (155 mg, 0.621 mmol) and dichlorobis(acetonitrile)palladium (19.9 mg, 13.7 μmol). After stirring the reaction mixture overnight at room temperature, ethyl acetate (11 ml) was added dropwise, thereby effecting precipitation of sodium salt of the compound of interest. Celite (0.8 g) was added to the mixture thus obtained. After filtration, the precipitate and celite were washed 3 times with ethyl acetate (2 ml). The precipitate was dissolved in water (3.0 ml) and washed 3 times with water (2.0 ml). The aqueous solution thus obtained was acidified with an ion exchange resin (manufactured by Mitsubishi Chemical Industries, Ltd.; trade name, DIAION PK216H) and mixed with acetone (7.5 ml). The ion exchange resin was separated by filtration and washed 3 times with acetone/water (2:1, 1.5 ml). The filtrates were combined, concentrated by evaporating acetone at 21° C. using an evaporator and then freeze-dried to obtain a light yellow powder (166 mg) with a yield of 85%.

Example 29

Removal of Allyl group from 3-O-allyl-1,2:5,6-di-O-isopropylidene-α-D-glucofuranose:

p-Toluenesulfinic acid (78.5 mg, 0.503 mmol) was added at room temperature to a solution of 3-O-allyl-1,2:5,6-di-O-isopropylidene-α-D-glucofuranose (136 mg, 0.452 mmol) prepared in Preparation 9 and tetrakis(triphenylphosphine)parlladium (36.6 mg, 31.7 μmol) in dichloromethane(4.5 ml). The reaction mixture was stirred at room temperature for 25 minutes and triethylamine (13 μl, 90 μmol) was added. The mixture was chromatographed on silica gel to give 1,2:5,6-di-O-isopropylidene-α-D-glucofuranose (117 mg) in 99% yield as white solids.

Example 30

Removal of Allyl group from N-allyl-N-phenylamine p-Toluenesulfinic acid (188 ml, 1.20 mmol) was added at room temperature to a solution of N-allyl-N-pentylphenylamine(221 mg, 1.08 mmol) and tetrakis(triphenylphosphine)palladium(87.8 mg, 75.9 μmol) in dichloromethane(11 ml). The reaction mixture was stirred at room temperature for 60 minutes and saturated aqueous sodium hydrogen carbonate(6.8 ml) was added. After stirred for 5 minutes, the mixture was extracted with ether(80 ml). The extract was dried on magnesium sulfate, filterd and concentrated in vacuum. The residue was chromatographed on silica gel to give N-pentylphenylamine(164 mg) in 93% yield as a colorless oil.

Example 31

Removal of allyl group from the compound, prepared in Preparation 13.

(2aE,4E,8E)-(4'R,5'S,6S,6'R,7S,11R,13S,15S, 17aR, 20aR,20bS)-6'-cyclohexyl-4',20b-dihydroxy-20-(2-propenyloxyimino)-5',6,8,19-tetramethyl-3',5',6,6',7,10,11,14,15, 17a,20,20a,20b-tridecahydro-17-oxospiro[11,15-methano-2H,13H,17H-furo[4,3,2-pq][2,6]benzodioxacyclooctadecin-13,2'-[2H]piran]-7-yl 2,6-dideoxy-4-O-(2,6-dideoxy-3-O-methyl-α-L-arabino-hexopyranosil)-3-O-methyl-α-L-arabino-hexopyranoside (53,0 mg, 54,0 μmol) prepared in Preparation 11 and toluenesulfinic acid (14.9 mg, 95.4 μmol) was dissolved in chloroform (550 μl). Tetrakis(triphenylphosphine)palladium (6.6 mg, 5.7 μmol) was added. After stirred for 1 hours at room temperature, the reaction solution was chromatographed on silica gel to give (2aE,4E,8E)-(4'R,5'S,6S,6'R, 7S,11R,13S,15S,17aR,20aR,20bS)-6'-cyclohexyl-4',20b-dihydroxy-20-(hydroxyimino)-5',6,8,19'-tetramethyl-3',5'6,6', 7,10,11,14,15,17a,20,20a,20b-tridecahydro-17-oxospiro[11, 15-methano-2H,13H,17H-furo[4,3,2-pq][2,6]benzodioxacyclooctadecin-13,2'-[2H]piran]-7-yl 2,6-dideoxy-4-O-(2,6-dideoxy-3-O-methyl-α-L-arabino-hexopyranosyl)-3-O-methyl-α-L-arabino-hexopyranoside (44.7 mg) in 89% yield.

Preparation 1

The chloroallyl esters or 2-methyl-2-propenyl esters of penem compounds used herein were prepared in a similar way to the process as described in International Publication No. WO88/08845 (Examples 1 to 11) without further purification.

Preparation 2

2-Propenyl 5R,6S-6-(1R-hydroxyethyl)-2-(1R-oxo-3S-thiolanylthio)-2-penem-3-carboxylate used herein was prepared in the following manner.

Sodium 5R,6S-6-(1R-hydroxyethyl)-2-(1R-oxo-3S-thiolanylthio)-2-penem-3-carboxylate (3.0 g, 8.08 mmol) was dissolved in N,N-dimethylformamide (25 ml) and allyl bromide (2.93 g, 24.2 mmol) was added. The reaction mixture was stirred at room temperature for 15 hours and poured into water (80 ml). After stirring for 2 hours, the resulting white solids were filtered off. The filtrate was extracted with methylene chloride (50 ml). The extract was washed with water (10 ml), dried over magnesium sulfate, filtered, concentrated and washed with ethyl acetate (5 ml) to give white solids. The white solids were combined, recrystallized from ethanol (30 ml) and filtered off to give the first crop of a propenyl ester. The mother liquor was concentrated and washed with ethyl acetate (2 ml) and dried in vacuum to give the second crop. The first and second crops were combined and dried in vacuum to give 2-propenyl 5R,6S-6-(1R- hydroxyethyl)-2-(1R-oxo-3S-thiolanylthio)-2-penem-3-carboxylate (2.17 g) as white solids in 69% yield.

Preparation 3

2-Butenyl 5R,6S-6-(1R-hydroxyethyl)-2-(1R-oxo-3S-thiolanylthio)-2-penem-3-carboxylate used herein was prepared in the following manner.

Sodium 5R,6S-6-(1R-hydroxyethyl)-2-(1R-oxo-3S-thiolanylthio)-2-penem-3-carboxylate (1.75 g, 4.71 mmol) was dissolved in N,N-dimethylformamide (5.2 ml) and 1-bromo-2-butene (1.91 g, 14.1 mmol) was added. The reaction mixture was stirred at room temperature for 20 hours and poured into water (50 ml). After stirring for 30 minutes, the light yellow solids were filtered off. The filtrate was extracted with methylene chloride (30 ml). The extract was dried over magnesium sulfate, filtered, concentrated and washed with ethyl acetate (5 ml) and n-hexane (5 ml) to give light yellow solids. The solids (2.0 g) were combined, recrystallized from ethanol (20 ml), filtered off and dried in vacuum to give 2-butenyl 5R,6S-6-(1R-hydroxyethyl)-2-(1R-oxo-3S-thiolanylthio)-2-penem-3-carboxylate (1.04 g) as white solids in 55% yield. The mother liquor was concentrated, washed with ethyl acetate (2 ml) and dried in vacuum to give the butenyl ester (0.24 g) as the second crop in 13% yield. The first and second crops were combined.

Preparation 4

Cinnamyl 5R,6S-6-(1R-hydroxyethyl)-2-(1R-oxo-3S-thiolanylthio)-2-penem-3-carboxylate was prepared in the following manner.

Sodium salt of 5R,6S-6-(1R-hydroxyethyl)-2-(1R-oxo-3S-thiolanilthio)-2-penem-3-carboxylic acid (6.88 g, 18.5 mmol) was dissolved in N,N-dimethylformamide (25 ml) to which was subsequently added cinnamyl bromide (3.65 g, 18.5 mmol). The reaction mixture was stirred at room temperature for 20 hours, poured into water (500 ml) and then extracted with methylene chloride (250 ml). The extract thus obtained was washed with water (50 ml) and concentrated. Isopropyl ether (200 ml) was added to the resulting residue, and the thus precipitated solid was collected by filtration. The solid was recrystallized from isopropanol (50 ml), collected by filtration and then dried in vacuo to obtain cinnamyl 5R,6S-6-(1R-hydroxyethyl)-2-(1R-oxo-3S-thiolanylthio)-2-penem-3-carboxylate (2.32 g) as a light yellow solid with a yield of 31%.

Preparation 5

2-Chloro-2-propenyl (2S,5R)-3,3-dimethyl-4,4,7-trioxo-4-thia(VI)-1-azabicyclo[3.2.0]heptane-2-carboxylate was prepared in the following manner.

Sodium 4,4-dioxo penicillanate (3.25 g, 12.7 mmol) and 1-bromo-2-chloro-2-propene (3.96 g, 25.5 mmol) in hexamethyl phosphoramide (26 ml) were stirred at 55° C. for 18 hours. This was mixed with ether (300 ml), washed 3 times with water (50 ml), dried on magnesium sulfate, filtered and then concentrated. The thus obtained residue thus obtained was dissolved in methanol (10 ml) and mixed with hexane (100 ml) to effect precipitation of solid material. After 15 minutes of stirring, the precipitate was collected by filtration, washed 3 times with hexane (10 ml) and then dried in vacuo to obtain 2-chloro-2-propenyl (2S,5R)-3,3-dimethyl-4,4,7-trioxo-4-thia(VI)-1-azabicyclo[3.2.0]heptane-2-carboxylate (3.36 g) as a white solid with a yield of 86%.

Preparation 6

2-Propenyl7-benzamido-3-acetoxymethyl-3-cepham-4-carboxylate was prepared in the following manner.

Tetrabutylammonium hydrogen sulfate (1.08 g, 3.19 mmol) was dissolved in water (4.6 ml), and the solution was adjusted to pH 6 with aqueous 5N sodium hydroxide solution. This was mixed with sodium 7-benzamido-3-acetoxymethyl-3-cepham-4-carboxylate (1.00 g, 2.51 mmol), stirred at room temperature for 2 hours while keeping the pH value at 6.6 using aqueous 1N sodium hydroxide solution and then extracted 3 times with chloroform (4.6 ml+2.3 ml×2). The chloroform extract was mixed with allyl bromide (912 mg, 7.53 mmol) and stirred at 50° C. for 2 hours. The reaction solution was poured into ethyl acetate (200 ml), washed 3 times with water (20 ml), dried on magnesium sulfate, filtered and then concentrated. The resulting residue was purified by a silica gel column chromatography to obtain 2-propenyl7-benzamido-3-acetoxymethyl-3-cepham-4-carboxylate (905 mg) as a light yellow viscous liquid with a yield of 87%.

Preparation 7

Allyl N-(p-methoxyphenyl) carbamate was prepared in the following manner.

Allyl chloroformate (1.45 g, 12.1 mmol) was added dropwise to dimethylacetamide (25 ml) solution of p-anisidine (1.24 g, 10.1 mmol) and N-ethylmorpholine (2.03 g, 20.1 mmol), which was cooled at −20° C. After 1 hour of stirring at −20° C., the reaction mixture was warmed to room temperature and poured into water (25 ml). This was extracted with ethyl acetate (250 ml). The ethyl acetate extract was washed with water (25 ml), dried on sodium sulfate, filtered and then concentrated. The resulting residue was purified by a silica gel column chromatography to obtain allyl N-(p-methoxyphenyl) (2.03 g) with a yield of 97%.

Preparation 8

3-O-Allyloxycarbonyl-1,2:5,6-di-O-isopropylidene-α-D-glucofuranose was prepared in the following manner.

At 0° C., allyl chloroformate (740 mg, 6.14 mmol) was added dropwise to methylene chloride (4 ml) solution of 4-dimethylaminopyridine (750 mg, 6.14 mmol) and 1,2:5,6-di-O-isopropylidene-α-D-glucofuranose (385 mg, 1.48 mmol). After warming up to room temperature and subsequently stirring for 3 hours, the reaction mixture was mixed with water (10 ml) and extracted with ether (85 ml). The ether extract was washed twice with water (10 ml), dried on magnesium sulfate, filtered and then concentrated. The resulting residue was purified by a silica gel column chromatography and then dried in vacuo to obtain 3-O-allyloxycarbonyl-1,2:5,6-di-O-isopropylidene-α-D-glucofuranose (509 mg) as a colorless transparent liquid with a quantitative yield.

Preparation 9

3-O-allyl-1,2:5,6-di-O-isopropylidene-α-D-glucofuranose used herein was prepared in the following manner.

Dimethyl sulfoxide (7.1 ml) was added at room temperature to sodium hydride (355 mg in 60% oil, 8.89 mmol, washed three times with n-hexane and dried in vacuum) and stirred for 10 minutes. 1,2:5,6-di-O-isopropylidene-α-D-glucofuranose (365 mg, 1.40 mmol) was added at room temperature to the mixture. The reaction mixture was stirred for 10 minutes and allylbromid(1.13 g, 9.33 mmol) was added. The mixture was stirred at room temperature for 2 hours, poured into water (10 ml), and extracted with ether (85 ml). The extract was washed twice with water (10 ml), dried over magnesium sulfate, filterd and dried in vacuum. The residue was chromatographed on silica gel to give 3-O-allyl-1,2:5,6-di-O-isopropylidene-α-D-glucofuranose (415 mg) in 99% yield as a colorless oil.

Preparation 10

N-Allyl-N-pentylphenylamine used herein was prepared in the following manner.

N-Allylphenylamine (1.95 g, 14.7 mmol) and bromopentane (2.22 g, 14.7 mmol) were stirred at 80° C. for 16 hours. After cooled to room temperature, the mixture was treated with a solution of sodium hydroxide(714 mg, 17.9 mmol) in water (1.5 ml), stirred for 30 minutes and extracted with ether (80 ml). The extract was dried over potassium carbonate, filterd and concentrated in vacuum. The residue was chromatographed on silica gel to give N-allyl-N-pentylphenylamine (1.68 g) in 56% yield as a colorless oil.

Preparation 11

(2aE,4E,8E)-(4'R,5'S,6S,6'R,7S,11R,13S,15S,17aR, 20aR, 20bS)-6'-cyclohexyl-4',20b-dihydroxy-20-(2-propenyloxyimino)-5',6,8,19'-tetramethyl-3',5',6,6',7,10,11,14,15, 17a,20,20a,20b-tridecahydro-17-oxospiro[11,15-methano-2H,13H,17H-furo[4,3,2-pq][2,6]benzodioxacyclooctadecin-13,2'-[2H]pyran]-7-yl 2,6-dideoxy-4-O-(2,6-dideoxy-3-O-methyl-α-L-arabino-hexopyranosil)-3-O-methyl-α-L-arabino-hexopyranoside used herein was prepared in the following manner.

(2aE,4E,8E)-(4'R,5'S,6S,6'R,7S,11R,13S,15S,17aR, 20aR,20bS)-6'-cyclohexyl-5',6,8,19-tetramethyl-3',5',6,6',7, 10,11,14,15,17a,20,20a,20b-tridecahydro-4',20,20b-trihydroxy-17-oxospiro[11,15-methano-2H,13H,17H-furo[4,3,2-pq][2,6]benzodioxacyclooctadecin-13,2'-[2H]pyran]-7-yl 2,6-dideoxy-4-O-(2,6-dideoxy-3-O-methyl-α-L-arabino-hexopyranosyl)-3-O-methyl-α-L-arabino-hexopyranoside (5.00 g, 5.47 mmol) was dissolved to methylene chloride (70 ml), and activated manganese dioxide (17.5 g, 0.201 mol) was added to it. Activated manganese dioxide (4.0 g, 46 mmol) was added twice to them at 15 hours later and at 20 hours later. After 23 hours, the reaction mixture was filtered and manganese dioxide was washed with ethylene chloride (100 ml). The filtrate and the washing liquid were concentrated in vacuum dried to give 20-oxo form (4.14 g) in 83% yield as light white yellow solids. The oxo form given above (800 mg, 878 μmol) was dissolved in methanol (6 ml) and dioxane (6 ml), and added at room temperature to a aqueous solution (6 ml). O-allylhydroxyamine hydrochloride (580 mg, 5.25 mmol) aqueous (6 ml) is dropped at room temperature. After stirred for 16 hours, the reaction solution was poured into water (30 ml). The white solid given was filtered and washed in water (15 ml). The extract was chromatographed on silica gel to give the target compound (520 mg) in 61% yield as white solid.

Preparation 12

Alkyl sulfinates were prepared in accordance with the procedure reported in [Synthesis, 584 (1990)]. Other sulfinates were prepared in the usual way by the reaction of sulfonyl chloride with sodium sulfite or zinc powder.

We claim:

1. A process for a removal of an allyl or allyloxycarbonyl group from an allyl or allyloxycarbonyl group protected compound, which comprises contacting the allyl or allyloxycarbonyl group protected compound with a sulfinic acid compound, in the presence of a palladium catalyst in a reaction-inert solvent.

2. A process according to claim 1 which comprises contacting said allyl or allyloxy group protected compound, wherein said allyl or allyloxy group protected compound comprises an allyl ester of a carboxylic acid, an allyloxycarbonyl derivative of an alcohol or an allyloxycarbonyl derivative of an amine with said sulfinic acid compound.

3. A process according to claim 2, wherein the sulfinic acid compound is represented by the formula:

     (I)

wherein X is $C_{1-20}$ alkyl, substituted $C_{1-20}$ alkyl (wherein the substituent(s) are independently halo, nitro, sulfo, oxo, amino, cyano, carboxy, hydroxy or moieties derived therefrom), phenyl, substituted phenyl (wherein the substituent(s) are independently $C_{1-3}$ alkyl, halo nitro, sulfo, oxo, amino, cyano, carboxy, hydroxy, acetamido or moieties derived therefrom), furyl or thienyl; and M is hydrogen, an alkali metal or ammonium salt residue.

4. A process according to claim 3, wherein X is phenyl or methylphenyl; and M is hydrogen, lithium, sodium, potassium or ammonium.

5. A process according to claim 3, wherein the sulfinic acid compound is lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid, ammonium benzenesulfinate, tetrabutylammonium benzenesulfinate, sodium p-carboxybenzenesulfinate, sodium octylsulfinate, sodium ethylsulfinate, sodium 4-chloro-3-nitrobenzenesulfinate, sodium 4-acetamidobenzenesulfinate, sodium thiophene-2-sulfinate, sodium methylsulfinate, sodium isobutylsulfinate, sodium hexadecylsulfinate, sodium hydroxymethanesulfinate, ammonium p-toluenesulfinate, triethylammonium p-toluenesulfinate or tetrabutylammonium benzenesulfinate.

6. A process according to claim 5, wherein the sulfinic acid compound is lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid or ammonium benzenesulfinate.

7. A process according to claim 2, wherein the palladium catalyst is a palladium compound capable of easily forming a π-allyl complex when reacted with an allyl compound.

8. A process according to claim 7, wherein the palladium catalyst is tetrakis(triphenylphosphine)palladium (0), dichlorobis(triphenylphosphine)palladium (II), dichlorobis(acetonitrile)palladium (II), dichlorobis(triisopropoxyphosphine)palladium (II), or palladium (II) diacetate.

9. A process according to claim 2, wherein the solvent is selected from alcohols, haloalkyl compounds, esters, ethers, nitriles, ketones, aromatic hydrocarbons, water and a mixture thereof.

10. A process according to claim 2, wherein the reaction is carried out at a temperature of −20° C. to 100° C.

11. A process according to claim 10, wherein the reaction is carried out at a temperature of 10° C. to 40° C.

12. A process according to claim 2 for the conversion of an allyl ester of a carboxylic acid to the carboxylic acid, wherein the carboxylic acid is a beta-lactam compound.

13. A process according to claim 12, wherein the carboxylic acid is a penam, cephem, carbapenem or penem compound.

14. A process according to claim 13 wherein said carboxylic acid is a penem compound and said penem is an allyl ester of 5R, 6S-6-(1R-hydroxyethyl)-2-(1R-oxo-3S-thiolanylthio)-2-penem-3-carboxylic acid, for the conversion of said allyl ester of 5R, 6S-6-(1R-hydroxyethyl)-2-(1R-oxo-3S-thiolanylthio)-2-penem-3-carboxylic acid to 5R, 6S-6-(1R-hydroxyethyl)-2-(1R-oxo-3S-thiolanylthio)-2-penem-3-carboxylic acid.

15. A process according to claim 1 wherein said allyl or allyloxycarbonyl group protected compound comprises an O-allylether of an alcohol, an N-allyl derivative of a compound containing an amino group or an O-allyl derivative of an oxime, which comprises contacting said O-allylether of said alcohol, said N-allyl derivative of said compound containing an amino group or said O-allyl derivative of said oxime with said sulfinic acid compound.

16. A process according to claim 15, wherein the sulfinic acid compound is represented by the formula:

     (I)

wherein X is $C_{1-20}$ alkyl, substituted $C_{1-20}$ alkyl (wherein the substituent(s) are independently halo, nitro, sulfo, oxo, amino, cyano, carboxy, hydroxy or moieties derived therefrom), phenyl, substituted phenyl (wherein the substituent(s) are independently $C_{1-3}$ alkyl, halo nitro, sulfo, oxo, amino, cyano, carboxy, hydroxy, acetamido or moieties derived therefrom), furyl or thienyl; and M is hydrogen, an alkali metal or ammonium salt residue.

17. A process according to claim 16, wherein X is phenyl or methylphenyl; and M is hydrogen, lithium, sodium, potassium or ammonium.

18. A process according to claim 16, wherein the sulfinic acid compound is lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid, ammonium benzenesulfinate, tetrabutylammonium benzenesulfinate, sodium p-carboxybenzenesulfinate, sodium octylsulfinate, sodium ethylsulfinate, sodium 4-chloro-3-nitrobenzenesulfinate, sodium 4-acetamidobenzenesulfinate, sodium thiophene-2-sulfinate, sodium methylsulfinate, sodium isobutylsulfinate, sodium hexadecylsulfinate, sodium hydroxymethanesulfinate, ammonium p-toluenesulfinate, triethylammonium p-toluenesulfinate or tetrabutylammonium benzenesulfinate.

19. A process according to claim 18, wherein the sulfinic acid compound is lithium p-toluenesulfinate, sodium p-toluenesulfinate, potassium p-toluenesulfinate, p-toluenesulfinic acid, ammonium p-toluenesulfinate, lithium benzenesulfinate, sodium benzenesulfinate, potassium benzenesulfinate, benzenesulfinic acid or ammonium benzenesulfinate.

20. A process according to claim 15, wherein the palladium catalyst is a palladium compound capable of easily forming a π-allyl complex when reacted with an allyl compound.

21. A process according to claim 20, wherein the palladium catalyst is tetrakis(triphenylphosphine)palladium (0), dichlorobis(triphenylphosphine)palladium (II), dichlorobis(acetonitrile)palladium (II), dichlorobis(triisopropoxyphosphine)palladium (II), or palladium (II) diacetate.

22. A process according to claim 15, wherein the solvent is selected from alcohols, haloalkyl compounds, esters, ethers, nitriles, ketones, aromatic hydrocarbons, water and a mixture thereof.

23. A process according to claim 15, wherein the reaction is carried out at a temperature of −20° C. to 100° C.

24. A process according to claim 23, wherein the reaction is carried out at a temperature of 10° C. to 40° C.

25. A process according to claim 15 for the conversion of an allyl ester of a carboxylic acid to the carboxylic acid, wherein the carboxylic acid is a beta-lactam compound.

26. A process according to claim 25, wherein the carboxylic acid is a penam, cephem, carbapenem or penem compound.

27. A process according to claim 26 wherein said carboxylic acid is a penem compound and said penem is an allyl ester of 5R, 6S-6-(1R-hydroxyethyl)-2-(1R-oxo-3S-thiolanylthio)-2-penem-3-carboxylic acid, for the conversion of said allyl ester of 5R, 6S-6-(1R-hydroxyethyl)-2-(1R-oxo-3S-thiolanylthio)-2-penem-3-carboxylic acid to 5R, 6S-6-(1R-hydroxyethyl)-2-(1R-oxo-3S-thiolanylthio)-2-penem-3-carboxylic acid.

28. A process according to claim 1 wherein said allyl or allyloxycarbonyl group protected compound is an O-allylether of an alcohol, an N-allyl derivative of a compound containing an amino group, an O-allyl derivative of an oxime and wherein said O-allylether of said alcohol is an O-allylether of a polyether, macrolide, oligosaccharide or glycoside and wherein said N-allyl derivative of said compound containing an amino group is an N-allyl derivative of an alkaloid, nucleoside or peptide and wherein said O-allyl derivative of said oxime is an O-allylether of a polyether, macrolide, oligosaccharide or glycoside.

* * * * *